(12) United States Patent
Hansen

(10) Patent No.: US 6,586,574 B1
(45) Date of Patent: Jul. 1, 2003

(54) STABILIZATION OF FREEZE-DRIED CAKE

(75) Inventor: Lars Lindgaard Hansen, Gadstrup (DK)

(73) Assignee: NN A/S, Bagsvaerd (DK)

( * ) Notice: Subject to any disclaimer, the term of this patent is extended or adjusted under 35 U.S.C. 154(b) by 0 days.

(21) Appl. No.: 09/638,590

(22) Filed: Aug. 15, 2000

Related U.S. Application Data
(60) Provisional application No. 60/150,985, filed on Aug. 26, 1999.

(30) Foreign Application Priority Data

Aug. 17, 1999 (DK) ........................................ 1999 01130

(51) Int. Cl.$^7$ ........................ A61K 35/14; A61K 38/36; C07K 1/06; C07K 14/745
(52) U.S. Cl. ........................ 530/384; 252/363.5; 514/2; 514/802; 514/834; 514/971
(58) Field of Search .................. 252/363.5; 514/834, 514/971, 802, 2; 530/384

(56) References Cited

U.S. PATENT DOCUMENTS

| | | | | |
|---|---|---|---|---|
| 3,773,626 A | | 11/1973 | Bernt et al. ........... 195/103.5 R |
| 4,297,344 A | * | 10/1981 | Schwinn et al. ......... 514/834 X |
| 4,687,664 A | * | 8/1987 | Philapitsch et al. ..... 530/384 X |
| 4,777,043 A | | 10/1988 | Bennett et al. .......... 424/94.64 |
| 4,877,608 A | * | 10/1989 | Lee et al. ................ 530/384 X |
| 5,824,639 A | * | 10/1998 | Berkner .................. 530/384 X |
| 5,917,021 A | | 6/1999 | Lee .......................... 530/387.3 |
| 6,310,183 B1 | * | 10/2001 | Johannessen et al. ....... 530/384 |

FOREIGN PATENT DOCUMENTS

EP 0 359 201 A2 3/1990

OTHER PUBLICATIONS

Toshiki Morichi, "Nature and Action of Protective Solutes in Freeze–Drying of Bacteria", National Institute of Animal Industry, Chiba, Japan, pp. 351–361 (1968).
Flandrois et al., Ann. Biol. Clin., vol. 47, pp. 252–260 (1989).
Davis et al., Archives of Biochemistry and Biophysics, vol. 311, pp. 307–312 (1994).

\* cited by examiner

*Primary Examiner*—Richard D. Lovering
(74) *Attorney, Agent, or Firm*—Richard W. Bork, Esq.; Reza Green, Esq.; Marc A. Began, Esq.

(57) ABSTRACT

The invention relates to the use of glycylglycine, optionally in combination with a sugar, and/or a sugar alcohol, and/or an amino acid, as a bulking agent in freeze-drying.

13 Claims, 1 Drawing Sheet

STABILIZATION OF FREEZE-DRIED CAKE

CROSS-REFERENCE TO RELATED APPLICATIONS

This application claims priority under 35 U.S.C. 119 of Danish application no. PA 1999 01130 filed on Aug. 17, 1999 and U.S. provisional application no. 60/150,985 filed on Aug. 26, 1999, the contents of which are fully incorporated herein by reference.

FIELD OF INVENTION

The present invention relates to the formation of freeze-dried cakes or plugs of stable structure by using glycylglycine as a freeze-drying cake-former or bulking agent. The invention further relates to a stabilised freeze-dried composition comprising proteins and glycylglycine.

BACKGROUND OF INVENTION

Proteins are relatively unstable in the aqueous state and undergo chemical and physical degradation resulting in a loss of biological activity during processing and storage. Lyophilisation or freeze-drying is a well-established method for preserving proteins for storage.

A lyophilisation cycle is usually composed of three steps: freezing, primary drying and secondary drying. In the freezing step, the protein solution is cooled until it is adequately frozen. Bulk water in the protein solution forms ice at this stage. This ice sublimes in the primary drying stage, which is conducted by reducing chamber pressure below the vapour pressure of the ice using a vacuum. Finally, sorber or bound water is removed at the secondary drying stage under reduced chamber pressure and elevated shelf temperature. The process produces a material known as a lyophilised cake. Prior to use the cake is reconstituted. The standard practice is to add back a volume of pure water.

In order to preserve protein conformation, activity and stability, the protein solution prone to be lyophilised usually contains agents facilitating this, so-called lyoprotectants and cryoprotectants. Cryoprotectants are agents which provide stability to the protein from freezing-induced stresses; however, the term also includes agents that provide stability, e.g. to bulk drug formulations during storage from non-freezing-induced stresses. Lyoprotectants are agents that provide stability to the protein during water removal from the system during the drying process, presumably by maintaining the proper conformation of the protein through hydrogen bonding. Cryoprotectants can also have lyoprotectant effects.

When water removal has taken place, the protein and agents are in the form of a dried "cake". This cake needs to have good properties as to form and structure, i.e. it must not collapse, as such collapsed cakes are hard or even impossible to dissolve (reconstitute) before use. One or more so-called bulking agents are added to the solution before lyophilisation. Bulking agents are agents which provide good lyophilised cake properties and which help the protein overcome various stresses associated with the lyophilisation process (for example shear/freezing). Bulking agents also help to form an pharmaceutically elegant product and help to maintain protein activity levels during the freeze-drying process and subsequent storage. Examples of frequently used bulking agents include mannitol, glycine, sucrose, lactose, etc. The agents also contribute to the tonicity of the formulations.

Therapeutic proteins for injection or infusion are often formulated and stored as lyophilised products. The lyophilised samples may be kept in long-term storage and reconstituted at a later time by adding a suitable administration diluent just prior to patient use.

High concentrations of salt in a sample will normally make the removal of water time consuming and difficult and it will be difficult to obtain a suitable freeze-dried cake.

There is still a need in the art for providing methods for improving freeze-drying processes and products, such as providing bulking agents that improve the properties of freeze-dried cakes or plugs.

It has now been found that glycylglycine can be used as a bulking agent in freeze-drying, giving structural stability to the freeze-dried plug or cake, and at the same time act as a stabiliser primarily against aggregation of proteins. Furthermore, by combining the functions as buffer substance (in solution before lyophilisation) and as bulking agent in one compound, the number of excipients in the freeze-dried formulation is reduced.

Glycylglycine can be used alone or in combinations with sugars, e.g. sucrose, and/or in combination with sugar alcohols, e.g. mannitol, and/or in combination with cyclodextrins, and/or amino acids, such as glycine or arginine. It has also been found that glycylglycine may advantageously be used as a freeze-drying cake-former when used in freeze-dried formulations containing high concentrations of salts (>5 mg/ml of salts).

PRIOR ART

Flandrois, C. et al., Annales de Biologie Clinique, Vol 47, pp. 252–260 (1989) relates to the use of glycylglycine as a buffer substance.

Davis, G. J. et al., Archives Biochem.Biophys., Vol.311, pp. 307–312 (1994) relates to the use of glycylglycine as a diagnostic reagent in the study of specific enzymatic reactions.

European Patent No. EP 359 201 B relates to the use of glycylglycine or glycylglycylglycine as a stabiliser of blood or plasma.

BRIEF DESCRIPTION OF THE INVENTION

Figure 1:
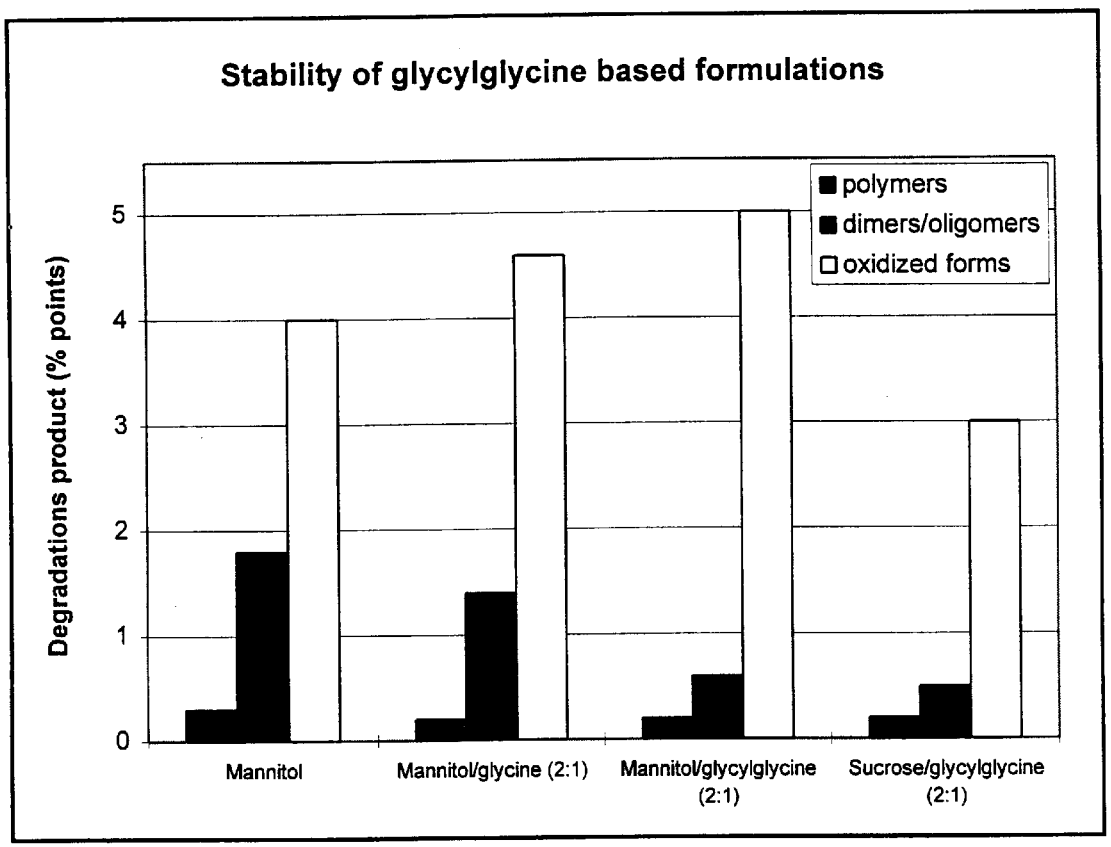
FIG. 1 shows the amounts of the degradation products of three different freeze-dried formulations of FFR-FVIIa.

The present invention provides a novel lyophilised composition comprising glycylglycine as a bulking agent.

In one aspect, the invention relates to a lyophilised composition in the form of a plug or cake, comprising glycylglycine as a bulking agent.

In one embodiment hereof, the composition further comprises one or more additional bulking agents. In an embodiment, the composition further comprises at least one sugar and/or at least one sugar alcohol and/or at least one amino acid.

In one embodiment, the bulking agent is mannitol or sucrose or histidine or a mixture of one or more of these in combination with glycylglycine.

In one embodiment, the bulking agent is glycylglycine in combination with mannitol. In another embodiment, the bulking agent is glycylglycine in combination with sucrose. In another embodiment, the bulking agent is glycylglycine in combination with histidine.

In one embodiment, the amount of glycylglycine to the total amount of additional bulking agent(s) is from 1:2 to 2:1 (w/w).

In another embodiment, the composition further contains a non-ionic surfactant.

In one embodiment, the non-ionic surfactant is a polysorbate or a poloxamer.

In one embodiment, the glycylglycine acts as a stabiliser of the plug or cake.

In one embodiment, the lyophilised composition is a lyophilised protein composition.

In one embodiment, the content of glycylglycine is at least 10 mg/ml of solution to be lyophilised. In another embodiment, the content of glycylglycine is at least 1% (w/w) (of solution to be lyophilised); in yet another embodiment, the content is at least 2% (w/w); in another embodiment, the content is at least 3% (w/w); in another embodiment, the content is at least 4% (w/w).

In one embodiment, the amount of glycylglycine is at least 10 mg/ml and the total amount of bulking agent is at least 2% (w/w) (of solution to be lyophilised). In another embodiment, the amount of glycylglycine is at least 13 mg/ml and the total amount of bulking agent is at least 2% (w/w). In another embodiment, the amount of glycylglycine is at least 10 mg/ml and the total amount of bulking agent is at least 3% (w/w). In another embodiment, the amount of glycylglycine is at least 10 mg/ml and the total amount of bulking agent is at least 4% (w/w). In another embodiment, the amount of glycylglycine is at least 13 mg/ml and the total amount of bulking agent is at least 3% (w/w). In another embodiment, the amount of glycylglycine is at least 13 mg/ml and the total amount of bulking agent is at least 4% (w/w). In another embodiment, the amount of glycylglycine is about 13 mg/ml and the total amount of bulking agent is about 4% (w/w).

In another aspect, the invention relates to the use of glycylglyeine as a freeze-drying cake-former or bulking agent.

In one embodiment, the invention relates to the use of glycylglycine as a freeze-drying cake-former or bulking agent in the lyophilisation of a protein solution.

In one embodiment, the solution to be lyophilised comprises at least 5 mg/ml of salt.

In one embodiment, the salt is an alkali metal salt or a calcium salt such as NaCl or $CaCl_2$.

In another embodiment, glycylglycine is used in combination with at least one sugar and/or at least one sugar alcohol and/or neutral salt and/or a non-ionic detergent.

In another aspect, the invention relates to a method for producing a lyophilised composition of a protein, comprising the following steps:

a) dissolving the protein in water or in a suitable aqueous buffer, optionally in the presence of one or more salts; and b) adding glycylglycine to the protein solution; and c) optionally adding at least one sugar and/or at least one sugar alcohol and/or a non-ionic detergent and/or a neutral salt to the solution; and d) freeze-drying the resulting solution; or a) dissolving glycylglycine in water or a suitable buffer; and b) adding the protein to the solution; and c) optionally adding at least one sugar and/or at least one sugar alcohol and/or a non-ionic detergent and/or a neutral salt to the solution; and d) freeze-drying the resulting solution; or a) dissolving glycylglycine in water or a suitable buffer, optionally in the presence of one or more salts; and b) optionally adding at least one sugar and/or at least one sugar alcohol and/or a non-ionic detergent and/or a neutral salt to the solution; and c) adding the protein to the solution; and d) freeze-drying the resulting solution.

DETAILED DESCRIPTION OF THE INVENTION

Glycylglycine has previously been used in low concentration (typically 10 mM–50 mM corresponding to less than 7 mg/ml) as a buffering substance in formulations of proteins. However, it has now been found that glycylglycine can be used as a bulking agent giving structural stability to the freeze-dried plug or cake and at the same time act as a stabiliser of proteins. Glycylglycine can be used alone or in combinations with sugars, e.g. sucrose, and /or in combination with sugar alcohols, e.g. mannitol, and/or in combination with cyclodextrins, and/or amino acids, such as glycine or arginine.

The glycylglycine should be present in an amount of at least 10 mg/ml, preferably at least 13 mg/ml.

It has also been found that glycylglycine can be used as a bulking agent or as a freeze-drying cake-former when high salt concentrations are present (>5 mg/ml of salts).

By combining the functions as buffer substance (in solution prior to lyophilisation) and as bulking agent in one compound, the number of excipients in the freeze-dried formulation is reduced. However, other suitable buffers may be used to formulate the solution before lyophilisation.

Throughout the present specification, the below terms have the following meaning: "Stabilising" means minimising the formation of aggregates (insoluble and/or soluble) and/or chemical degradation as well as provide lyoprotection and cryoprotection of the protein, maintenance of pH, and proper conformation of the protein during storage so that substantial retention of biological activity and protein stability is maintained. By "structural stabilisation" or "structural stability" is meant the ability to form a lyophilised plug or cake with good properties and looks, i.e., that it does not collapse and is readily dissolved before use.

Protein stability can be affected inter alia by such factors as ionic strength, pH, temperature, repeated cycles of freeze/thaw and exposures to shear forces. Active protein may be lost as a result of physical instabilities, including denaturation and aggregation (both soluble and insoluble aggregate formation), as well as chemical instabilities, including, for example, hydrolysis, deamidation, and oxidation, just to name a few. For a general review of stability of protein pharmaceuticals, see, for example, Manning, et al., Pharmaceutical Research 6:903–918 (1989).

"Storage-stable" means the product is stabilised for storage at temperatures between 5° C.–25° C. and remains within product specifications for a suitable time period—often several months "Bulking agent" generally includes agents which provide good lyophilised cake properties, which form an pharmaceutically elegant product, which help the protein overcome various stresses (shear/freezing for example) associated with the lyophilisation process, and which help to maintain protein activity levels during the freeze-drying process and subsequent storage. Examples of often-used bulking agents include mannitol, glycine, sucrose, lactose, etc. The agents contribute to the tonicity of the formulations.

"Cryoprotectants" generally includes agents which provide stability to the protein from freezing-induced stresses;

however, the term also includes agents that provide stability, e.g. to bulk drug formulations during storage from non-freezing-induced stresses. Examples of cryoprotectants include polyols such as, for example, mannitol, and include saccharides such as, for example, sucrose, as well as including surfactants such as, for example, polysorbate, poloxamer or polyethylene glycol, and the like. Cryoprotectants also contribute to the tonicity of the formulations.

The term "lyoprotectant" includes agents that provide stability to the protein during water removal from the system during the drying process, presumably by maintaining the proper conformation of the protein through hydrogen bonding. Examples of lyoprotectants include saccharides and di- or trisaccharides. Cryoprotectants may also have lyoprotectant effects. While preferred concentrations range from about 0.5 to 2%, relatively higher concentrations (for example 5%) are suitable as the levels used are limited only by those customarily used in clinical practice.

The term "surfactants" generally include those agents, which protect the protein from air/solution interface-induced stresses and solution/surface induced-stresses (e.g. resulting in protein aggregation), and may include detergents such as polysorbate, poloxamer or polyethylene glycol, and the like. Optionally, concentrations from about 0.01% to about 1% (w/w) are suitable for maintaining protein stability, however, the levels used in actual practice are customarily limited by clinical practice.

The term "buffering agent" or "buffer" encompasses those agents which maintain the solution pH in an acceptable range prior to lyophilisation and may include histidine, phosphate, citrate, tris, diethanolamine, and the like. The upper concentration limits are generally higher for "bulk" protein than for "dosage" protein forms as is readily appreciated by one skilled in the art. For example, while buffer concentrations can range from several millimolar up to the upper limit of their solubility (e.g., histidine could be as high as 200 mM), one skilled in the art would also take into consideration achieving/maintaining an appropriate physiologically suitable concentration. Percentages are weight/weight when referring to solids and weight/volume when referring to liquids.

The term "isotonic", 300±50 mOsM, is meant to be a measure of osmolality of the protein solution prior to lyophilisation; reconstitution is typically with water for injection (WFI). Maintaining physiological osmolality is important for the dosage formulations. However for bulk formulations, much higher concentrations can be effectively utilised as long as the solution is made isotonic prior to use.

The term "excipients" includes pharmaceutical acceptable reagents to provide good lyophilised cake properties (bulking agents) as well as provide lyoprotection and cryoprotection of the protein, maintenance of pH, and proper conformation of the protein during storage so that substantial retention of biological activity and protein stability is maintained.

"Proteins" include, but are not limited to blood coagulation factors, e.g. Factor IX, Factor VIII, Factor VII, activated Factor VII (FVIIa), protein C; growth hormones, e.g. human growth hormone (hGH), bovine GH, porcine GH; GLP-1, heparin binding protein (HBP); insulin or insulin variants, modified Factor VII and obvious variants hereof.

"Modified factor VII or VIIa" is coagulation factor VII (in zymogenic or activated form) having at least one modification in its catalytic centre, which modification substantially inhibits the ability of the modified Factor VII to activate plasma Factor X or IX. (See WO 92/15686, WO 94/27631, WO 96/12800 and WO 97/47651 (Novo Nordisk/ZymoGenetics), which is hereby incorporated by reference)

As used herein, FFR-FVIIa concentration is conveniently expressed as mg/ml or as U/ml, with 1 mg/ml approximately equal to 20 U/ml.

| Abbreviations | |
|---|---|
| FVII | Coagulation factor VII in its single chain form |
| FVIIa | Coagulation factor VII in its cleaved, activated two-chain form |
| rFVII (rFVIIa) | Recombinant factor VII (recombinant factor VIIa) |
| FVIIai | Modified factor VII which is coagulation factor VII having at least one modification in its catalytic centre, which modification substantially inhibits the ability of the modified Factor VII to activate plasma Factor X or IX. |
| RFVIIai | Recombinant modified factor VIIa (recombinant FVIIai) |
| TF | Tissue Factor |
| DEGR-FVIIa (DEGR-FVII) | Coagulation factor FVIIa (FVII) wherein the catalytic centre has been inactivated by chemically reacting FVIIa (FVII) with Dansyl-Glu-Gly-Arg chloromethylketone (DEGR-cmk) |
| FFR-FVIIa (FFR-FVII) | Coagulation factor FVIIa (FVII) wherein the catalytic centre has been inactivated by chemically reacting FVIIa (FVII) with Phe-Phe-Arg chloromethylketone (FFR-cmk) |
| PPA-FVIIa (PPA-FVII) | FVIIa (FVII) reacted with D-Phe-Pro-Arg chloromethylketone (PPA-cmk) |
| DEGR-cmk | Dansyl-Glu-Gly-Arg chloromethylketone |
| FFR-cmk | D-Phe-Phe-Arg or Phe-Phe-Arg chloromethylketone |
| PPACK | D-Phe-Pro-Arg chloromethylketone (PPA-cmk) |
| DFFR-cmk | Dansyl-D-Phe-Phe-Arg or dansyl-Phe-Phe-Arg chloromethylketone |
| Ser344-FVIIa (Ser344-FVII) | Coagulation factor FVIIa (FVII) wherein the catalytic centre has been inactivated by replacing the native amino acid in position 344 with serine. |
| Gly-gly | glycylglycine |

Preferred buffers used (when preparing the solution to be freeze-dried) are glycine, histidine, arginine, glycylglycine, citrate, carbonate and phosphate, more preferred are glycine, histidine, arginine and glycylglycine, most preferred are glycylglycine. The preferred concentration range is from 0.66 mg/ml–1.32 mg/ml for the buffering effect alone.

Further stabilisation of the freeze-dried protein can be obtained by the addition of surfactants, e.g. polysorbate or poloxamer such as Tween 20, Tween 80, or poloxamer 188. Preferred detergents are poloxamers, e.g. Poloxamer 188, Poloxamer 407; alkyl ethers e.g. Cremophor A25, Sympatens ALM/230; and polysorbates/Tweens, e.g. Polysorbate 20, Polysorbate 80. More preferred are Poloxamers, e.g. Poloxamer 188, and Tweens, e.g. Tween 20 and Tween 80. Typically, the detergents are added in an amount of from 0.005 to 5 mg/ml. Preferred amounts are from 0.01 to 3 mg/ml, more preferred from 0.01 to 0.3 mg/ml for Tween 20 and/or Tween 80 and from 0.05 to 3.0 mg/ml for Poloxamer 188.

Preferred sugars, sugar alcohols and amino acids to be used in combination with glycylglycine are sucrose, dextrose, lactose, maltose, cyclodextrins, maltodextrins, and dextrans; mannitol, and polyethylene glycols; glycine, arginine, and histidine. More preferred are sucrose, cyclodextrins, maltose, and lactose; mannitol; glycine, histidine and arginine. Even more preferred are sucrose, mannitol and histidine, alone or in combination. The combinations of mannitol with glycylglycine and sucrose with glycylglycine are most preferred.

A bulking agent is normally present in an amount of from about 20 mg/ml to about 250 mg/ml. According to the present invention, the bulking agent should be present in an amount of from about 15 mg/ml to about 250 mg/ml (in the solution of protein ready to be lyophilised), preferably in an amount of at least 20 mg/ml. If glycylglycine is the sole bulking agent, glycylglycine is preferably present in an amount of from about 15 to about 250 mg/mg, more preferred from about 20 to about 250 mg/ml, more preferred from about 25 to about 250 mg/ml, more preferred from about 25 to about 100 mg/ml, more preferred from about 25 to about 40 mg/ml.

If glycylglycine acts as a bulking agent in combination with a sugar, a sugar alcohol or an amino acid or a mixture thereof, the total amount of agents should preferably be from about 15 mg/ml to about 250 mg/mg, more preferred from about 20 to about 250 mg/ml, more preferred from about 25 to about 250 mg/ml, more preferred from about 25 to about 100 mg/ml, more preferred from about 25 to about 40 mg/ml. The amount of glycylglycine should be at least 10 mg/ml.

Preferably, the ratio between glycylglycine and the total amount of additional agents (sugar, sugar alcohol and/or amino acid) is from 4:1 to 1:4, more preferred from 3:1 to 1–3, even more preferred from 1:2 to 2:1 (glycylglycine:other (w/w)).

Preferred is a combination of glycylglycine with mannitol comprising at least 27 mg/ml of mannitol and comprising from 13 mg/ml of glycylglycine to a total of at least 40 mg/ml of bulking agent. Preferred is also a combination of glycylglycine with sucrose comprising at least 27 mg/ml of sucrose and comprising from 13 mg/ml of glycylglycine to a total of at least 40 mg/ml of bulking agent. Preferred is also a combination of glycylglycine with histidine comprising at least at least 27 mg/ml of histidine and comprising from 13 mg/ml of glycylglycine to a total of at least 40 mg/ml of bulking agent It has furthermore been found that glycylglycine alone or a mixture containing glycylglycine may advantageously be used as a freeze-drying cake-former when freeze-drying formulations containing high salt concentrations (>5 mg/ml of salts).

Proteins suitable for freeze-drying in combination with glycylglycine are, for example, blood coagulation factors (e.g. FIX, FVIII, FVII, FVIIa), growth hormone (e.g. human GH), GLP-1, heparin binding protein (HBP), insulin or insulin variants, modified FVII/FVIIa. Preferred are hGH, FIX, FVIII, FVII/FVIIa and modified FVII/FVIIa, FVIIa and modified FVII/FVIIa being the most preferred.

A storage-stable composition according to the invention consists essentially of protein, glycylglycine, and, optionally, at least one neutral salt, and/or at least one sugar, and/or at least one sugar alcohol, and/or at least one amino acid, and/or a non-ionic detergent.

Preparation of freeze-dried protein/manufacturing

The active ingredient e.g. in the form of a dry solid or a frozen liquid is prepared for the preparation of the formulated bulk material used for freeze-drying. If the active ingredient, hereafter called the bulk material, is a frozen liquid the liquid is thawed. The formulation additives are either dissolved directly into the liquid bulk or a concentrated dilution buffer containing the formulation additives is mixed with bulk. The bulk is diluted in order to obtain the desired protein concentration.

If the bulk substance is a dry substance it may be dissolved directly into a solution containing the formulation additives yielding the desired protein concentration. The formulated bulk is sterile filtered and filled into lyophilisation vials with stoppers placed in the half-closed position. Cooling is put on the shelves of the freeze-drier in order to freeze the vials and the product below critical product temperatures. Water is removed by introducing vacuum and condensation of water vapour on the ice-condenser of the freeze-drier. When the product is dry, usually less 1% residual moisture content, the vials are closed and capped. Manufacturing is finalised.

Pharmaceutical compositions

Lyophilised formulations according to the present invention, when formulated with pharmaceutical proteins, may be reconstituted and administered to a patient. They may also be reconstituted and reformulated into other pharmaceutical compositions, e.g. further containing pharmaceutically acceptable auxiliary substances as described below, which composition, in turn, may be liquid or freeze-dried and reconstituted before use.

The reconstituted formulations are intended for parental administration for prophylactic and/or therapeutic treatment. Preferably, the pharmaceutical compositions are administered parentally, i.e., intravenously, subcutanously, or intramuscularly, or they are administered by way of continuous or pulsative infusion.

The compositions are reconstituted using an acceptable (sterile) diluent or carrier, preferably an aqueous carrier. A variety of aqueous carriers may be used, e.g., water (e.g. Water For Injection/WFI), buffered water, saline (e.g. 0.4% saline), glycine (e.g. 0.3% glycine), and the like. The reconstitution diluent may also contain one or more salts, such as a calcium salt (e.g. $CaCl_2$) or a combination of a sodium and a calcium salt (e.g. NaCl and $CaCl_2$).

When the protein is FVIIa or modified FVIIa, preferred salts are $CaCl_2$ and NaCl, a preferred amount is around 1.47 mg/ml for $CaCl_2$ and from 1.75–2.92 mg/ml for NaCl.

The compositions may contain further pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. The concentration of protein in such formulations can vary widely, i.e., from less than about 0.5%, usually at or at least about 1% to as much as 15 or 20% by weight. Primarily fluid volumes, viscosities, etc., in accordance with the selected particular mode of administration will select the concentration of protein.

Thus, reconstituting a composition according to the invention in sterile Ringer's solution could make up a typical pharmaceutical composition for intravenous infusion. Actual methods for preparing compositions for parental administration will be known or apparent to those skilled in the art and are described in more detail in for example, *Remington. The Science and Practice of Pharmacy,* 19th ed., Mack Publishing Company, Easton, Pa. (1995).

The pH of reconstituted compositions should be within a range of pharmaceutically acceptable values, typically from 5–8. Preferably, the pH is between 5.5–7.5.

The following examples are offered by way of illustration, not by way of limitation.

EXAMPLES

Example 1

Screening of Bulking Agents

In this example ALL formulations had the same composition prior to the addition of bulking agents: 1 mg/ml modified rFVIIa, 1.75–2.95 mg/ml NaCl, 1.47 mg/ml CaCl$_2$, glycylglycine 1.32 mg/ml (buffering agent).

| | Evaluation of the freeze-dried product: OK = nice freeze-drying cake or plug, OK+ = as "OK" with improved stability, C = Collapsed freeze-drying cake | | |
|---|---|---|---|
| Bulking agents | As the sole bulking agent | In combination with glycylglycine | Optimal range: concentration (ratios of excipient to glycylglycine) |
| Glycylglycine | OK+ | | 25–40 mg/ml |
| Mannitol | OK | OK+ | 40 mg/ml (2:1) |
| Sucrose | C | OK+ | 40 mg/m/ (2:1) |
| Glycine | OK | not tested with glycylglycine | 25–40 mg/ml |
| Arginine | C | not tested with glycylglycine | not optimal |
| Histidine | C | not tested with glycylglycine | not optimal |

The table shows the effect of glycylglycine alone and in combination with other excipients. It is seen that addition of glycylglycine is superior to some amino acids like arginine and histidine in providing cake structure stability and it is seen that addition of glycylglycine to sucrose gives structural stability to the collapsed cake obtained by freeze-drying of sucrose alone.

Example 2

Physical and Chemical Stability of Formulations Stabilised With Glycylglycine

In this example ALL formulations had the same composition prior to the addition of bulking agents: 1 mg/ml modified rFVIIa, 1.75–2.95 mg/ml NaCl, 1.47 mg/ml CaCl$_2$, glycylglycine 1.32 mg/ml (buffering agent). Either Tween 80 or Poloxamer 188 was added as surfactant. The formulations has been stored under at accelerated conditions for up to 4 weeks

| | dimers | | polymers | | oxidation products | |
|---|---|---|---|---|---|---|
| Bulking agent | t = 0 | t = 4 weeks | t = 0 | t = 4 weeks | t = 0 | t = 4 weeks |
| Mannitol (3:0) | <0.3% | 1,8% | <0.3% | 0.3% | 2,4% | 4.0% |
| Mannitol/glycine (2:1) | <0.3% | 1.4% | <0.3% | <0.3% | 2.5% | 4.6% |
| Mannitol/glycylglycine (2:1) | <0.3% | 0.6% | <0.3% | <0.3% | 2.4% | 5.0% |
| sucrose/glycylglycine (2:1) | <0.3% | 0.5% | <0.3% | <0.3% | 2.3% | 3.0% |
| glycylglycine (3:0)[1] | 0.3%–<0.3% | 0.4%–1.9% | 0.4%–<0.3% | 0.4% | 2.1%–2.2% | 4.7%–6.2% |

[1]Data for 0.1 mg/ml to 1.0 mg/ml content of Poloxamer 188.

1) Data for 0.1 mg/ml to 1.0 mg/ml content of Poloxamer 188.

Example 3

Further Stabilisation of the Formulations With Surfactants

The effect of surfactants on protein stability have initially been performed on the reference formulations defined as the formulation containing mannitol as the sole bulking agent. The effect of Tween 20 and Tween 80 on this formulation was quite similar, whereas the same effect could be obtained with Poloxamer 188 at a slightly higher surfactant concentration. The effect of surfactants seems to be quite general on all formulations tested and the optimal concentration range is defined as from 0.01–0.3 mg/mL for the Tween 20 and/or Tween 80 and from 0.05–3.0 mg/ml for Poloxamer 188.

| | Absorbance (turbidity) at 340 nm | | Visual evaluation of solution | |
|---|---|---|---|---|
| Formulation | no surfactant | with surfactant | no surfactant | with surfactant |
| mannitol | 0.150 | 0.044 | unclear | clear |
| Mannitol/glycylglycine | 0.123 | 0.044 | unclear | clear |
| glycylglycine | 0.164 | 0.049 | unclear | clear | pH = 6.5 and surfactant = 0.05–0.1 mg/ml of Tween 80

Example 4

In this example all PLACEBO formulations had the same composition prior to the addition of bulking agents: 2.95 mg/ml NaCl, 1.47 mg/ml CaCl$_2$, glycylglycine 1.32 mg/ml (buffering agent). In this case NO PROTEIN was added to the formulations.

| | Evaluation of the freeze-dried product: OK = nice freeze-drying cake, C = Collapsed freeze-drying cake | | |
|---|---|---|---|
| Bulking agents | As the sole bulking agent | In combination with glycylglycine | Optimal range: concentration (ratios of excipient to glycylglycine) |
| Glycylglycine | OK | | 40 mg/ml (3:0) |
| Mannitol | OK | OK | 40 mg/ml (2:1) |
| Sucrose | C | C (partly collapsed) | 40 mg/ml (2:1) |

Example 5

Four formulations containing mannitol, mannitol/glycine (2:1), mannitol/glycylglycine (2:1) and sucrose/glycylglycine (2:1), respectively, as bulking agents, were prepared and the amounts of degradation products in formulations containing glycylglycine were compared to formulations without glycylglycine. ALL formulations had the same composition prior to the addition of bulking agents: 1 mg/ml modified rFVIIa, 1.75–2.95 mg/ml NaCl, 1.47 mg/ml CaCl$_2$, glycylglycine 1.32 mg/ml (buffering agent). Either Tween 80 or Poloxamer 188 was added as surfactant.

The formulations has been stored under at accelerated conditions for up to 4 weeks and the results shown represents the data collected after 4 weeks of storage.

| | Degradation products (% points) | | |
|---|---|---|---|
| Bulking agents | polymers | dimers/oligomers | oxidized forms |
| Mannitol | 0.3 | 0.8 | 4.0 |
| Mannitol/glycine (2:1) | 0.2 | 1.3 | 4.6 |
| Mannitol/glycylglycine (2:1) | 0.2 | 0.6 | 5.0 |

-continued

| Bulking agents | Degradation products (% points) | | |
| --- | --- | --- | --- |
| | polymers | dimers/oligomers | oxidized forms |
| Sucrose/glycylglycine (2:1) | 0.2 | 0.5 | 3.0 |

This is illustrated in FIG. 1.

What is claimed is:

1. A lyophilized composition comprising a protein and glycylglycine as a bulking agent, wherein said composition is obtainable by lyophilizing a solution containing said protein and at least 10 mg/ml of glycylglycine.

2. The composition of claim 1, wherein said protein is activated Factor VII.

3. The composition of claim 1, wherein said protein is modified Factor VII.

4. A composition according to claim 1, which comprises one or more additional bulking agents.

5. The composition according to claim 4, wherein the amount of glycylglycine to the total amount of additional bulking agent(s) is from 1:2 to 2:1 (w/w).

6. The composition according to claim 4, which comprises at least one sugar and/or at least one sugar alcohol and/or at least one amino acid.

7. The composition according to claim 6, wherein the bulking agent is mannitol or sucrose or histidine or a mixture of one or more of these in combination with glycylglycine.

8. The composition according to claim 7, wherein the bulking agent is glycylglycine in combination with mannitol.

9. The composition according to claim 7, wherein the bulking agent is glycylglycine in combination with sucrose.

10. A method for producing a lyophilized composition, said method comprising the step of lyophilizing a solution containing at least 10 mg/ml of glycylglycine as a bulking agent.

11. The method of claim 10, wherein the solution to be lyophilized further contains a protein.

12. The method of claim 11, wherein said protein is activated Factor VII.

13. The method of claim 11, wherein said protein is modified Factor VII.

* * * * *